United States Patent
Koskela et al.

(10) Patent No.: US 6,810,874 B1
(45) Date of Patent: *Nov. 2, 2004

(54) POWDER INHALER FOR COMBINED MEDICAMENT

(75) Inventors: Tommi Koskela, Kuopio (FI); Antti Koivisto, Kuopio (FI); Matti Silvasti, Kuopio (FI); Jussi Haikarainen, Helsinki (FI)

(73) Assignee: Innovata Biomed Limited, Edinburgh (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/959,319

(22) PCT Filed: Apr. 20, 2000

(86) PCT No.: PCT/FI00/00348

§ 371 (c)(1),
(2), (4) Date: Jan. 18, 2002

(87) PCT Pub. No.: WO00/64520

PCT Pub. Date: Nov. 2, 2000

(30) Foreign Application Priority Data

Apr. 23, 1999 (FI) ................................................ 990914

(51) Int. Cl.⁷ ........................................... A61M 16/00
(52) U.S. Cl. .............................. 128/203.15; 128/203.19
(58) Field of Search ....................... 128/200.11–200.13, 128/200.17–200.19, 200.21, 200.22, 200.23, 200.24, 203.12, 203.15, 203.19, 203.21; 604/58, 62, 64

(56) References Cited

U.S. PATENT DOCUMENTS

| | | | | |
|---|---|---|---|---|
| 3,874,381 A | * | 4/1975 | Baum ..................... | 128/200.14 |
| 5,002,048 A | * | 3/1991 | Makiej, Jr. ............. | 128/200.23 |
| 5,007,419 A | * | 4/1991 | Weinstein et al. ..... | 128/200.23 |
| 5,169,029 A | * | 12/1992 | Behar et al. ................... | 222/1 |
| 5,524,613 A | | 6/1996 | Haber et al. | |
| 5,575,280 A | * | 11/1996 | Gupte et al. ........... | 128/203.15 |
| 5,664,557 A | * | 9/1997 | Makiej, Jr. ............. | 128/200.23 |
| 5,857,457 A | * | 1/1999 | Hyppola ................ | 128/203.15 |
| 5,904,139 A | * | 5/1999 | Hauser ................... | 128/200.23 |
| 5,941,241 A | * | 8/1999 | Weinstein et al. ..... | 128/200.23 |
| 6,543,443 B1 | * | 4/2003 | Klimowicz et al. .... | 128/200.23 |
| 6,553,987 B1 | * | 4/2003 | Davies .................. | 128/200.14 |
| 2003/0116157 A1 | * | 6/2003 | Braithwaite et al. ... | 128/203.15 |
| 2003/0136406 A1 | * | 7/2003 | Seppala ................. | 128/203.15 |

* cited by examiner

Primary Examiner—Teena Mitchell
(74) Attorney, Agent, or Firm—Finnegan, Henderson, Farabow, Garrett & Dunner, LLP

(57) ABSTRACT

The invention relates to a multidose powder inhaler for the dispensing of a powdered medicament by inhalation. The device comprises two or more medicament containers for different drug powders which are inhaled as a combined medication. The device of the invention is useful, for example, in the treatment of asthma.

3 Claims, 5 Drawing Sheets

POWDER INHALER FOR COMBINED MEDICAMENT

This application is a national stage filing of PCT International Application No. PCT/FI00/00348, filed on Apr. 20, 2000, which published in the English language. This application also claims the benefit of priority under 35 U.S.C. §119(a) to Finnish patent application no. 990914, filed on Apr. 23, 1999.

BACKGROUND OF THE INVENTION

The present invention relates to a device for dispensing of a powdered drug preparation by inhalation. The device is in particular a multiple-dose device without propellant gas, equipped with a metering means, which dispenses doses from a powder container. The device comprises two or more powder containers for different drug powders which can be inhaled as a combined medication. The device of the invention is useful, for example, in the treatment of asthma.

The administering of a powdered drug preparation by inhalation from an inhaler is known. Multiple-dose type powder inhalers comprising a flow container which holds the drug and a metering member which measures and dispenses a unit dose are also known, for example from patent publications GB 2165159, EP 79478, and EP 166294. In these devices, a series of dosing recesses are notched into the surface of a cylindrical metering member, and the said member is disposed in a chamber of precisely the same shape. When the metering member is rotated, the dosing recesses in turn will move first to a position in alignment with the powder container for being filled and thereafter to a position in alignment with the inhalation channel, whereupon a unit dose will fall by gravity from the dosing recess into the inhalation channel. Thereafter the dose of medicament is inhaled from the inhalation channel. These devices have the drawback that they make overdosing of the medicament possible by allowing the dispensing of a plurality of doses in succession into the inhalation channel, whereby a multiple dose may be drawn by one inhalation.

Attempts have been made to solve the above-mentioned problem by using dispensing systems in which the dosing recess will not be emptied into the inhalation channel by gravity but, instead, the dose of medicament is inhaled directly from the dosing recess, as disclosed in patent publications WO 92/00771 and WO 92/09322. When the metering member is rotated, the dosing recesses will move first to a position in alignment with the flow container for filling, and then to the inhalation channel, which is shaped so that the dosing recess will be emptied under the effect of the air flow being inhaled, and thereafter, having rotated through a full 360°, back to a position in alignment with the flow container.

In the treatment of respiratory disorders it is often beneficial to administer a combination of drugs, e.g. combination of a bronchodilator and an anti-inflammatory drug to a patient. The devices described above are not capable to deliver more than one drug powder at a time. Even though it is in some cases possible to mix two or several drugs to a inhalable powder mixture to be administered simultaneously as a single dose, the incompatibility of the drug substances, interactions during storage or different aerosolization properties may often prevent the use of such drug mixture. Therefore, in order to inhale a combined medication a patient may have to inhale different drug powders from two powder inhalers. A multi-container powder inhaler has been earlier described in U.S. Pat. No. 5,524,613. However, this device is complex and requires a pressurized air source to aid the inhalation process.

Therefore, there is a need for a simple low-cost multi-dose powder inhaler, which is able to deliver a combined medication by a single inhalation

SUMMARY OF THE INVENTION

The present invention is related to a multi-dose powder inhaler capable of delivering a combined medicament, e.g. bronchodilator and an anti-inflammatory drug, simultaneously by a single inhalation. Rather than having a powder container for a mixture of the active ingredients, the inhaler comprises two powder containers from which doses needed for the combined administration are metered, brought to the air channel and inhaled simultaneously. Preferably the two containers contain different active ingredients. The active ingredients are in the separate containers, are brought to the air channel by separate dosing recesses and are mixed not earlier than in the air channel or in the respiratory tract of the patient during inhalation. Furthermore the inhaled air stream can be conducted via two separate aerosolization channels, one for each medicament powder. Accordingly, the differences in the aerosolization properties of each medicament powder can be taken into account and each aerosolization channel can be designed according to the properties of each medicament powder.

The inhaler of the present invention is able to deliver and deaggregate medicament powder from two or more dosing recesses simultaneously without the use of pressurized air even if used by a patient having reduced inhalation capacity.

DETAILED DESCRIPTION OF THE INVENTION

Figure 1:
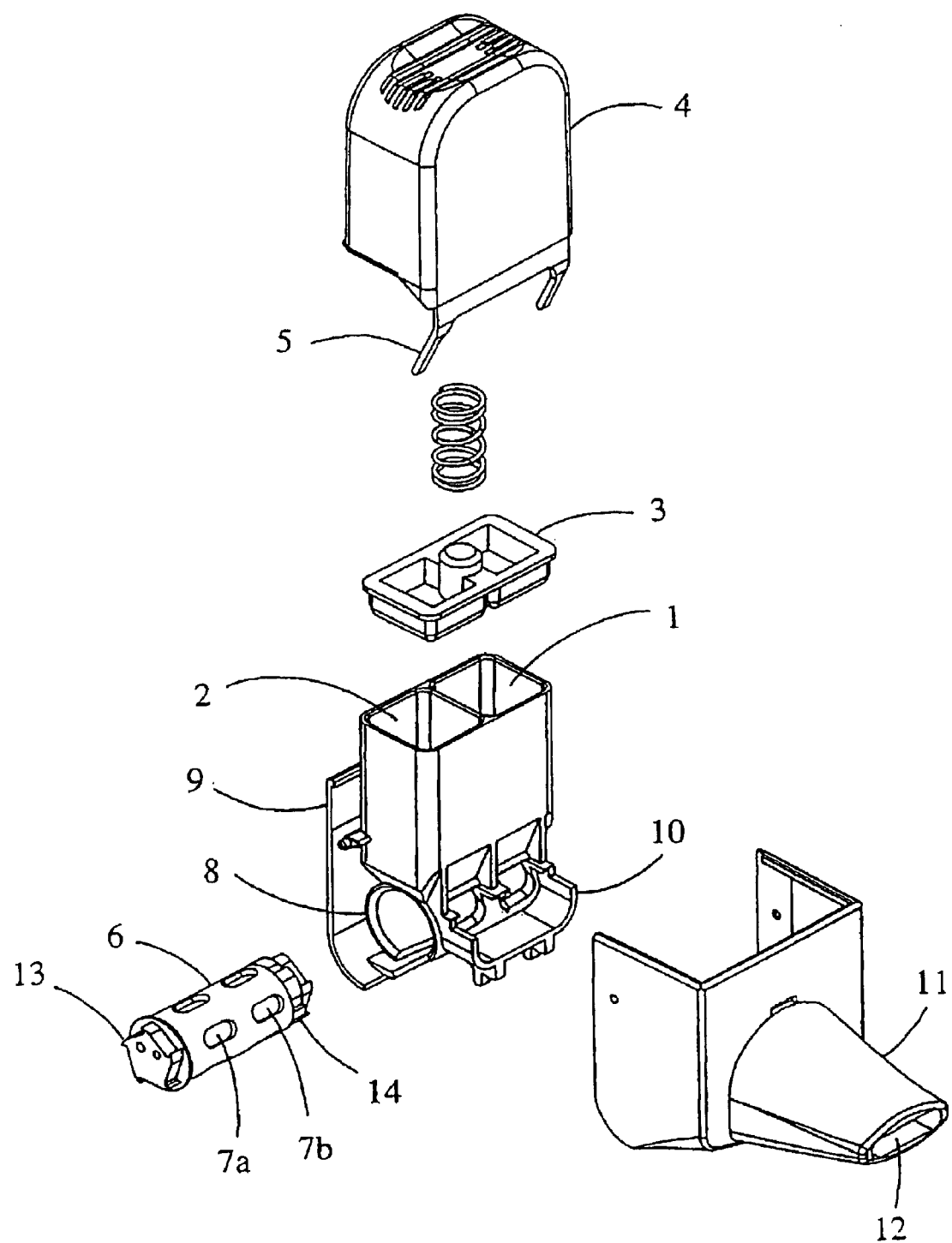
FIG. 1 is an explosive perspective view of one embodiment of the device of the invention.

The invention relates to a device for dispensing powdered medicament by inhalation, comprising a first and a second medicament container for receiving a plurality of medicament doses; an air channel through which air is drawn via a mouthpiece; a metering member in the form of a rotatable metering drum equipped with a first and a second dosing recess for receiving in one position a metered dose of the powdered medicament from the first and the second medicament container and for bringing in another position the metered dose of the powdered medicament from the first and the second medicament container to the air channel where the powdered medicament is aerosolized upon inhalation simultaneously from the first and the second dosing recess. In a preferred embodiment the air channel is conducted via two separate aerosolization channels.

The first and the second medicament containers are separated so that the active ingredients can not be mixed during storage. The containers contain, in the powder form, preferably different active ingredients which are to be delivered to a patient as a combined medication. Such combined medication can be a combination of any two drugs which can be administered by inhalation. In the treatment of asthma a typical combination is a combination of a bronchodilator and an anti-inflammatory drug. The anti-inflammatory drug is preferably a steroidal anti-inflammatory drug. Suitable drug combinations include e.g. formoterol and budesonide, salmeterol and beclomethasone dipropionate, and salmeterol and fluticasone propionate. Normally, the container has a supply of medicament for e.g. 200 doses.

The metering member is in a form of a rotatable drum, e.g. a cylinder, and is equipped with two series of dosing recesses notched into the surface of the metering member. In the first position of the metering member the first dosing recess is in alignment with the first medicament container and, simultaneously, the second dosing recess is in alignment with the second medicament container for being filled with the powder. When the metering member is rotated to the second position, the first and the second dosing recesses are moved to the air channel. The first and the second dosing recess may be of different size and/or shape according to the properties of each powder.

The air channel is preferably designed so that at the beginning of the inhalation air is led directly into the filled dosing recesses which are then intensively flushed by the inflowing air, and the powder is aerosolized simultaneously from the first and the second dosing recesses. As the powder is aerosolized directly from the dosing recesses, the possibility of overdosing by inhaling multiple doses is avoided.

In a preferred embodiment the inhaled air stream is conducted via two separate aerosolization channels, one for each medicament powder. The cross-sectional shape and dimensions of each aerosolization channel can then be designed according to the aerosolization and deaggregation properties of each medicament powder, e.g. to produce different air flow resistance for each medicament powder. If two separate aerosolization channels are used, the two active ingredients are mixed with each other not earlier than in the mouthpiece or, if the separate aerosolization channels are led throughout the mouthpiece, in the mouth of the patient.

The device of the invention is further illustrated below by way of example, with reference to FIGS. 1 to 5d.

In FIG. 1 the structure of one embodiment of the device of the invention is shown in an explosive view. The first and second medicament containers (1, 2) which are to be filled with the powdered medicament, have a square cross-section and conical end portions. A lid (3) closes the upper edge of the medicament containers. The cover (4) together with a flap (5), the function of which will be explained below, is adapted to cover the medicament containers (1, 2) and the lid (3). A manually rotatable metering drum (6) having two series of five dosing recesses (7a, 7b) is mounted to the hollow cylindrical body (8), which is moulded together with the medicament containers (1, 2).

Moulded together with the medicament containers is also the rear wall (9) of the device as well as the projection (10) to receive the mouthpiece (11) with the air channel (12). The metering drum (6) has, in addition to the series of dosing recesses, teeth (13) which are engaged with the flap (5). The device is actuated by pressing down the cover, whereby the flap (5) engaged with the teeth (13) causes the metering member rotate so that rotation can only be accomplished stepwise corresponding to the peripheral distance between the dosing recesses. The detent drive of the metering member automatically aligns the dosing recesses with the outlet of the medicament container on the one side and the air channel of the mouthpiece on the other side. Furthermore, the cylindrical body has an extended detent nose (not shown) which engages into notches (14) in the metering drum such that analogue to a ratchet rotation is only possible to one direction.

Figure 2:
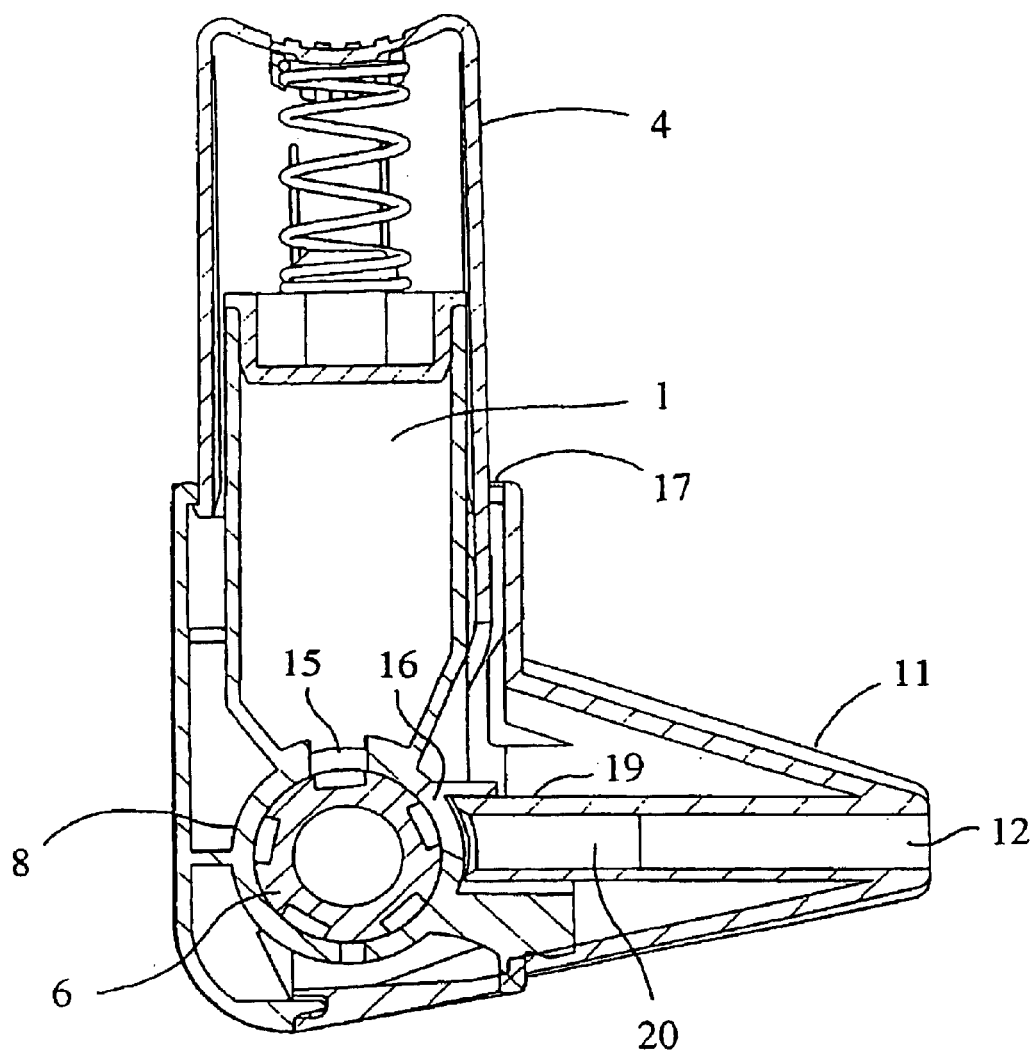
FIG. 2 is a longitudinal section of the device through a first medicament container.

FIG. 2 shows a longitudinal section through the first medicament container of one embodiment of the device is shown. The cylindrical body (8) has an opening (15) through which powder can fall from the medicament container to the dosing recess when the dosing recess is in alignment with the opening (15). Another opening (16) is provided at the level of the air channel (12) for discharging the powder from the dosing recess to the air channel upon inhalation. In the position shown in FIG. 2 the upper dosing recess is just being filled with the dose of the first medical powder from the first medicament container, while the earlier filled dosing recess has turned to the air channel and is ready to be inhaled. The mouthpiece (11), through which the medical powder can be inhaled, is formed at one side of the inhalation device and has an air channel (12) for distribution of the dose of medicament from the dosing recess into the flow of breathing air. In the area where the mouthpiece is attached, air intakes (17) are provided. The intaken air is led to a slot between the opening (16) of the cylindrical body and a partition wall (19) of the mouthpiece. The slot, which is preferably moulded as a nozzle, provides strongly aligned stream of air to the dosing recess blowing the powder out from the dosing recess into the air channel without leaving any residue.

Figure 3C:
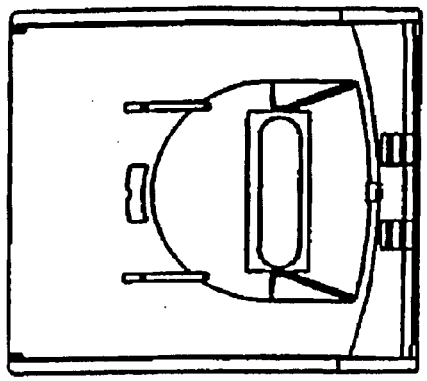
FIGS. 3a, 3b, 3c and 3d are a front view, a cross section viewed from the side, back view and a cross section viewed from above, of one embodiment of the mouth piece.
Figure 3B:
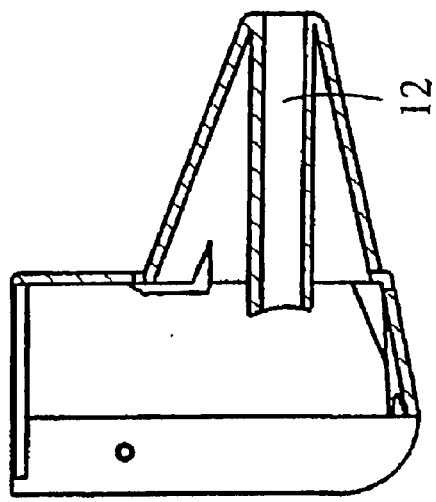
Figure 3A:
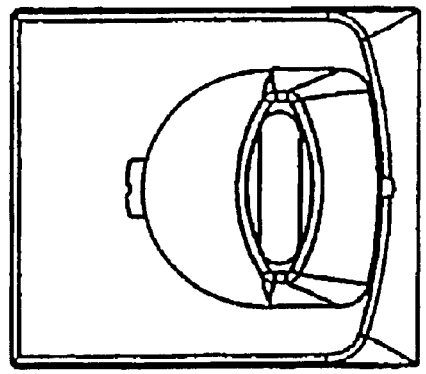
Figure 3D:
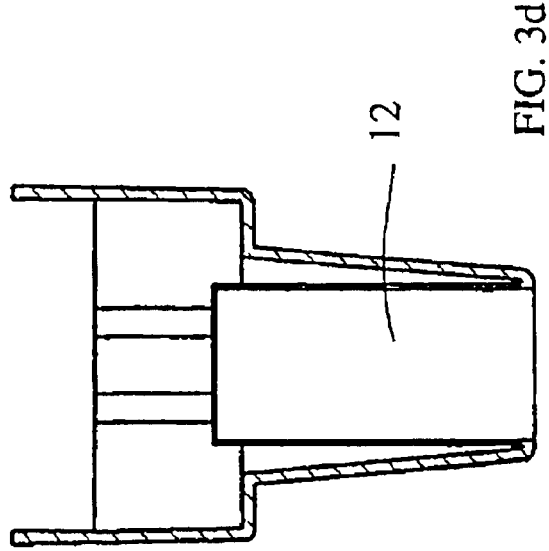

FIGS. 3a, b, c and d show one embodiment of the mouthpiece having a wide air channel (12) covering both the first and the second dosing recesses. In this embodiment the active ingredients are mixed with each other as soon as they are aerosolized from the dosing recesses.

Figure 4C:
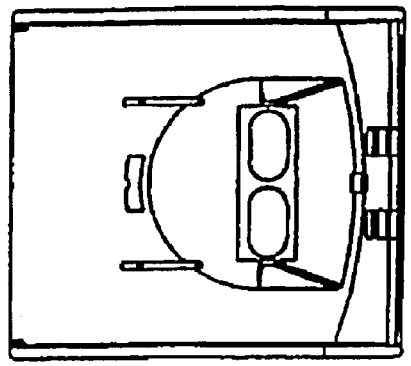
FIGS. 4a, 4b, 4c and 4d are a front view, a cross section viewed from the side, back view and a cross section viewed from above, of a second embodiment of the mouth piece.
Figure 4B:
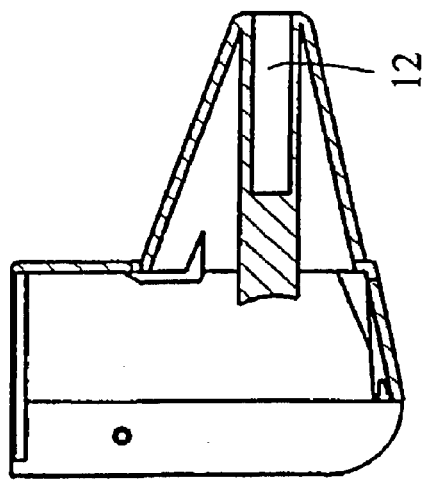
Figure 4A:
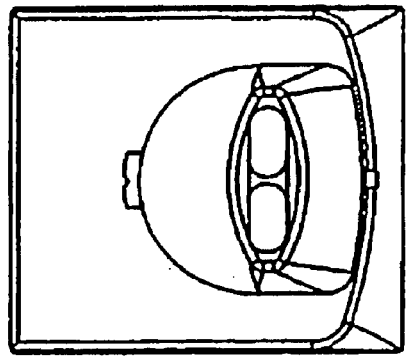
Figure 4D:
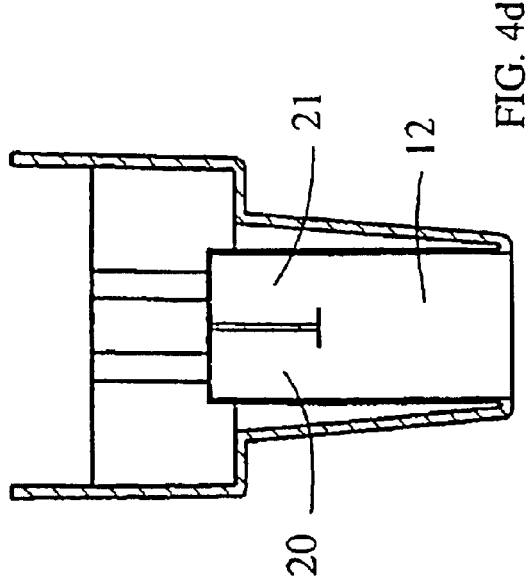

FIGS. 4a, b, c and d show another embodiment of the mouthpiece, where the air channel (12) comprises two separate aerosolization channels (20, 21) which are united in the mouthpiece to the main air channel. In this embodiment the active ingredients are mixed with each other not earlier than in the main air channel in the mouthpiece.

Figure 5C:
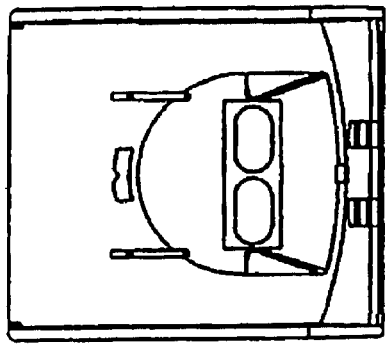
FIGS. 5a, 5b, 5c and 5d are a front view, a cross section viewed from the side, back view and a cross section viewed from above, of a third embodiment of the mouth piece.
Figure 5B:
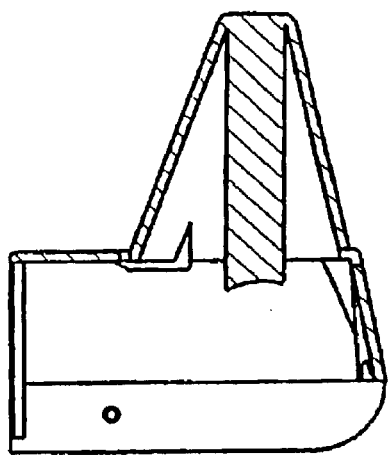
Figure 5A:
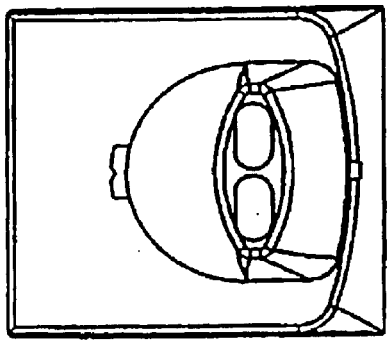
Figure 5D:
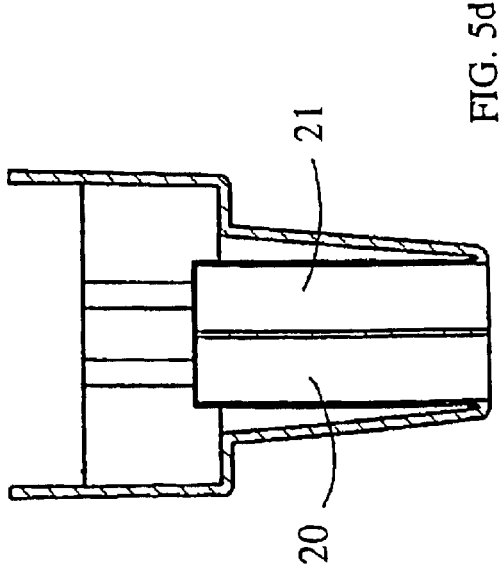

FIGS. 5a, b, c and d show yet another embodiment of the mouthpiece, where the air channel comprises two separate aerosolization channels (20, 21), which are led throughout of the mouthpiece. In this embodiment the active ingredients are mixed with each other not earlier than in the mouth or respiratory tract of the patient.

Other modifications and variations can be made to the disclosed embodiments without departing from the subject of the invention as defined in the following claims. For example, more than two medicament containers and corresponding series of dosing recesses could be used. In addition, a counter could be mounted to the inhaler to count the number of rotations of the dosing member. It is considered to be routine for one skilled in the art to make such modifications to the device of the invention.

What is claimed is:

1. A device for dispensing powdered medicament by inhalation, comprising a first and a second medicament container for receiving a plurality of medicament doses; an air channel through which air can be drawn via a mouthpiece; a metering member in the form of a rotatable metering drum equipped with a first and a second dosing recess for receiving in one position a metered dose of powdered medicament from the first and from the second medicament container and for bringing in another position the metered doses of powdered medicament from the first and the second medicament container to the air channel where the powdered medicament is aerosolized upon inhalation simultaneously from the first and the second dosing recess.

2. A device of claim 1 wherein the air channel comprises two separate aerosolization channels.

3. A device of claim 2, wherein the two separate aerosolization channels are led throughout the mouthpiece.

* * * * *